US010471283B2

(12) United States Patent
Kohli et al.

(10) Patent No.: US 10,471,283 B2
(45) Date of Patent: *Nov. 12, 2019

(54) COMPOSITIONS AND METHODS FOR THE TREATMENT OF XEROSTOMIA

(75) Inventors: Rajnish Kohli, Hillsborough, NJ (US); Richard Scott Robinson, Belle Mead, NJ (US); Richard J. Sullivan, Atlantic Highlands, NJ (US); Diane Cummins, Livingston, NJ (US); Nagaraja Jayaraman, New York, NY (US); MaryAnn Filadelfi-Keszi, Wilmington, DE (US)

(73) Assignee: Colgate-Palmolive Company, New York, NY (US)

( * ) Notice: Subject to any disclaimer, the term of this patent is extended or adjusted under 35 U.S.C. 154(b) by 210 days.

This patent is subject to a terminal disclaimer.

(21) Appl. No.: 12/866,630

(22) PCT Filed: Feb. 6, 2009

(86) PCT No.: PCT/US2009/033291
§ 371 (c)(1),
(2), (4) Date: Aug. 6, 2010

(87) PCT Pub. No.: WO2009/100265
PCT Pub. Date: Aug. 13, 2009

(65) Prior Publication Data
US 2011/0189110 A1    Aug. 4, 2011

Related U.S. Application Data

(60) Provisional application No. 61/027,438, filed on Feb. 9, 2008, provisional application No. 61/027,442, filed on Feb. 9, 2008, provisional application No. 61/027,432, filed on Feb. 8, 2008, provisional application No. 61/027,431, filed on Feb. 8, 2008, provisional application No. 61/027,420, filed on Feb. 8, 2008, provisional application No. 61/027,435, filed on Feb. 8, 2008.

(51) Int. Cl.
| | |
|---|---|
| *A61K 31/198* | (2006.01) |
| *A61K 8/19* | (2006.01) |
| *A61K 8/21* | (2006.01) |
| *A61K 8/24* | (2006.01) |
| *A61Q 11/00* | (2006.01) |
| *A61K 8/44* | (2006.01) |
| *A61K 9/00* | (2006.01) |

(52) U.S. Cl.
CPC ........... *A61Q 11/00* (2013.01); *A61K 8/44* (2013.01); *A61K 9/00* (2013.01); *A61K 31/198* (2013.01)

(58) Field of Classification Search
CPC .......... A61K 31/198; A61K 8/19; A61K 8/21; A61K 8/24
See application file for complete search history.

(56) References Cited

U.S. PATENT DOCUMENTS

| | | | |
|---|---|---|---|
| 3,235,459 A * | 2/1966 | Francis | ................. 424/52 |
| 3,535,421 A | 10/1970 | Briner et al. | |
| 3,538,230 A | 11/1970 | Pader et al. | |
| 3,678,154 A | 7/1972 | Widder et al. | |
| 3,696,191 A | 10/1972 | Weeks | |
| 3,862,307 A | 1/1975 | Digiulio | |
| 3,925,543 A | 12/1975 | Donohue | |
| 3,932,605 A | 1/1976 | Vit | |
| 3,932,608 A | 1/1976 | Anderson et al. | |
| 3,937,807 A | 2/1976 | Haefele | |
| 3,943,241 A | 3/1976 | Anderson et al. | |
| 3,959,458 A | 5/1976 | Agricola et al. | |
| 3,988,434 A | 10/1976 | Schole et al. | |
| 3,991,177 A | 11/1976 | Vidra et al. | |
| 4,011,309 A | 3/1977 | Lutz | |
| 4,022,880 A | 5/1977 | Vinson et al. | |
| 4,025,616 A | 5/1977 | Haefele | |
| 4,042,680 A | 8/1977 | Muhler et al. | |
| 4,051,234 A | 9/1977 | Gieske et al. | |
| 4,058,595 A | 11/1977 | Colodney | |
| 4,064,138 A | 12/1977 | Saari et al. | |
| 4,100,269 A | 7/1978 | Pader | |
| 4,108,979 A | 8/1978 | Muhler et al. | |
| 4,108,981 A | 8/1978 | Muhler et al. | |
| 4,146,607 A | 3/1979 | Ritchey | |
| 4,154,813 A | 5/1979 | Kleinberg | |
| 4,154,815 A | 5/1979 | Pader | |
| 4,160,821 A | 7/1979 | Sipos | |
| 4,216,961 A | 7/1980 | Curtis et al. | |
| 4,225,579 A | 9/1980 | Kleinberg | |
| 4,259,316 A | 3/1981 | Nakashima et al. | |
| 4,269,822 A | 5/1981 | Pellico et al. | |
| 4,305,928 A | 12/1981 | Harvey | |

(Continued)

FOREIGN PATENT DOCUMENTS

| | | |
|---|---|---|
| CN | 1156022 | 8/1997 |
| CN | 1671400 | 9/2005 |

(Continued)

OTHER PUBLICATIONS

US 5,989,525 A, 11/1999, Kleinberg et al. (withdrawn)
Ettinger RL. "Xerostomia: A Symptom Which Acts Like a Disease". Age and Ageing. 1996; 25:409-412.*
International Search Report and Written Opinion in International Application No. PCT/US09/033291, dated Sep. 19, 2009.
Machado et al. CaviStat Confection Inhibition of Caries in Posterior Teeth, Abstract, 83rd Session of the American Association for Dental Research, Mar. 21-24, 2007, New Orleans, LA.

(Continued)

*Primary Examiner* — Jeffrey S Lundgren
*Assistant Examiner* — Chris E Simmons

(57) ABSTRACT

The present invention is directed to methods and compositions comprising a basic amino acid, e.g., arginine, for the treatment of dry mouth.

16 Claims, No Drawings

(56) References Cited

U.S. PATENT DOCUMENTS

| | | | |
|---|---|---|---|
| 4,335,102 | A | 6/1982 | Nakashima et al. |
| 4,339,432 | A | 7/1982 | Ritchey et al. |
| 4,340,583 | A | 7/1982 | Wason |
| 4,355,022 | A | 10/1982 | Rabussay |
| RE31,181 | E | 3/1983 | Kleinberg et al. |
| 4,466,954 | A | 8/1984 | Ichikawa et al. |
| 4,477,429 | A | 10/1984 | Silbering et al. |
| 4,528,181 | A | 7/1985 | Morton et al. |
| 4,532,124 | A | 7/1985 | Pearce |
| 4,538,990 | A | 9/1985 | Pashley |
| 4,645,662 | A | 2/1987 | Nakashima et al. |
| 4,656,031 | A | 4/1987 | Lane et al. |
| 4,725,576 | A | 2/1988 | Pollock et al. |
| 4,820,506 | A | 4/1989 | Kleinberg et al. |
| 4,842,847 | A | 6/1989 | Zahid |
| 4,866,161 | A | 9/1989 | Sikes et al. |
| 4,885,155 | A | 12/1989 | Parran, Jr. et al. |
| 4,992,420 | A | 2/1991 | Neeser |
| 4,997,640 | A | 3/1991 | Bird et al. |
| 5,000,939 | A | 3/1991 | Dring et al. |
| 5,004,597 | A | 4/1991 | Majeti |
| 5,096,700 | A | 3/1992 | Seibel et al. |
| 5,286,480 | A | 8/1994 | Boggs et al. |
| 5,334,617 | A | 12/1994 | Ulrich et al. |
| 5,370,865 | A | 12/1994 | Yamagishi et al. |
| 5,496,558 | A | 3/1996 | Napolitano et al. |
| 5,639,795 | A | 6/1997 | Friedman et al. |
| 5,693,795 | A | 6/1997 | Friedman et al. |
| 5,747,004 | A | 5/1998 | Giani et al. |
| 5,762,911 | A | 6/1998 | Kleinberg et al. |
| 5,906,811 | A | 5/1999 | Hersh |
| 5,922,346 | A | 7/1999 | Hersh |
| 5,997,301 | A | 12/1999 | Linden |
| 6,217,851 | B1 * | 4/2001 | Kleinberg et al. ............ 424/49 |
| 6,436,370 | B1 | 8/2002 | Kleinberg et al. |
| 6,488,961 | B1 | 12/2002 | Robinson et al. |
| 6,524,558 | B2 | 2/2003 | Kleinberg et al. |
| 6,524,588 | B1 | 2/2003 | Kleinberg et al. |
| 6,558,654 | B2 | 5/2003 | McLaughlin |
| 6,805,883 | B2 | 10/2004 | Chevaus et al. |
| 2002/0064504 | A1 | 5/2002 | Kleinberg et al. |
| 2002/0081360 | A1 | 6/2002 | Burgard et al. |
| 2005/0215473 | A1 | 9/2005 | Alvarez et al. |
| 2006/0094643 | A1 | 5/2006 | Svirkin et al. |
| 2007/0053849 | A1 * | 3/2007 | Doyle ..................... A61K 8/02 424/50 |
| 2007/0154863 | A1 | 7/2007 | Cai et al. |
| 2007/0286820 | A1 | 12/2007 | Prencipe et al. |

FOREIGN PATENT DOCUMENTS

| | | |
|---|---|---|
| CN | 1701815 | 11/2005 |
| EP | 1806134 | 7/2007 |
| GB | 2354441 | 3/2001 |
| JP | 7258053 | 10/1995 |
| WO | WO 2000/078270 | 12/2000 |
| WO | WO 06/013081 | 2/2006 |
| WO | WO 06/073417 | 7/2006 |
| WO | WO 2007/107929 | 9/2007 |
| WO | WO2009100267 | 8/2009 |

OTHER PUBLICATIONS

Chatterjee et al,. Bacterial Acidification and CaviStat Alkalinization of Occlusal Fissure pH, Abstract, 83rd Session of the American Association for Dental Research, Mar. 9-12, 2005, Baltimore, MD.

Kleinberg I., A Mixed-Bacteria Ecological Approach to Understanding the Role of the Oral Bacteria in Dental Caries Causation: An Alternative to *Streptococcus mutans* and the Specific-Plaque Hypothesis, Crit. Rev. Oral Biol. Med,. 12(2): 108-125 (2002).

Kleinberg I., A New Salvia-Based Anticaries Composition, Dentistry Today, vol. 18, No. 2, Feb. 1999.

Abdollahi et al., 2000, "L-Arginine/Nitric Oxide Pathway and Interaction with Lead Acetate on Rat Submandibular Gland Function", Pharmacology & Toxicology, 87(5):198-203.

dentistryiq.com, 2005, www.dentistry.com/index/display/article-display/223252/articles/dental-economics/online-stories/new-candy-counteracts-tooth-decay-strengthens-teeth.html.

Dmitrenko, 2008, "Arginine: Biological Effect, Influence on Nitric Oxide Synthesis", UCJ, 1-2(22):137-140.

Mashkovsky, 2001, "Novaya Volna", Drugs,Physician's Handbook, 2:122-126.

Ortek, 2001, findarticles.com/p/articles/mi_mOEIN/is_2001_April_19/ai_73388103/"Ortek Announces Issuance of Second U.S. Patent for Non-Anti-Cavity Agent.", last paragraph of p. 3.

Ortek, 2002, Packaging with ingredient list for ProClude® (launched Jul. 2002).

Ortek, 2004, Packaging with ingredient list for DenClude® (launched Dec. 2004).

Perio-Talk, 2006, www.perio-talk.com/2006/05/heard-that-treating-sensitive-teeth.html.

Preetha et al., 2005, "Comparison of Artificial Saliva Substitutes", Trends Biomater. Artif, Organs, 18(2):178-186.

Queiroz et al., 2007, "Electrochemical Behavior and pH Stability of Artificial Salivas for Corrosion Tests", Braz. Oral Res., 21(3):209-215.

Spolsky et al., 2007, "Products—Old, New, and Emerging", CDA Journal, 35:731-737—Dry Mouth Considerations.

Takeda et al., 2003, "Possible Role of Nitric Oxide in Radiation-Induced Salivary Gland Dysfunction", Radiation Research, 159(4):465-470—abstract.

State University of New York Health Sciences Center, 2002, Stony Brook Dentistry Today 3(1):1-20 http://alumniandfriends.stonybrook.edu/document.doc?id=57.

DenClude Desensitizing Dental Cream, 2007, http://www.colgateprofessional.com/LeadershipUS/Docs/DenClude_DataSheet.pdf.

Wiesenfeld et al., 1983, "A critical assessment of oral lubricants in patients with xerostomia," Br. Dent. J. 155(5):155-157.

Kleinberg, 2002, "SensiStat: A new saliva-based composition for simple and effective treatment of dentinal sensitivity pain," Dentistry Today website http://www.dentistrytoday.com/restorative/1824.

\* cited by examiner

COMPOSITIONS AND METHODS FOR THE TREATMENT OF XEROSTOMIA

This application claims the benefit of U.S. Patent Application Ser. No. 61/027,438 filed Feb. 9, 2008, and also claims the benefit of U.S. Patent Application Ser. No. 61/027,442 filed Feb. 9, 2008, and U.S. Patent Application Ser. Nos. 61/027,432; 61/027,431; 61/027,420; and 61/027,435 all filed Feb. 8, 2008, the contents of which applications are all incorporated herein by reference.

BACKGROUND OF THE INVENTION

Dry mouth or xerostomia is an acute or chronic condition primarily caused by the lack of saliva. It may be caused by an underlying disease, such as Sjögren's syndrome, dehydration, trauma to the salivary glands, consumption of alcohol, or a side effect to medications. It has been identified as a condition increasing in the general population. Roughly 15% to 20% of young adults complain of oral dryness, and 30-40% of people ages 60-80 complain of oral dryness.

Xerostomia may cause several complications in patients. Saliva may be decreased, and may be foamy, thick and ropy. The tongue may be dry, fissured, lobulated, and may be infected with various bacteria and yeasts. Cheeks are often dry, dull and pale. The decreased moisture in the mouth creates difficulties in eating, as the chewing and swallowing of food is exacerbated by the lack of saliva. This also interferes with a person's ability to taste food, and produce speech. Furthermore, a moist mouth is beneficial in intimate human relations, which may also suffer as a result of dry mouth.

Patients suffering from xerostomia also suffer from extensive dental decay, e.g., caries, including areas not usually prone to decay, such as the lower incisors and roots. One possible explanation is that pellicle, which is present in saliva, provides a protective barrier between acids and a tooth surface, and such a barrier is reduced in the absence of saliva.

There are numerous products available to alleviate dry mouth, including oral moisturizing rinses, gels and synthetic saliva sprays, but there are few products which provide an anticaries effect. Current oral products for the treatment of dry mouth require high concentrations of fluoride to lower their risk of developing caries.

There is a continuing need to develop oral care compositions and methods to treat people suffering from dry mouth. There is also a continuing need to develop oral care compositions and methods to inhibit the development of caries in persons suffering from dry mouth. There is also a continuing need to develop oral care compositions which may aid in the consumption of foods, and production of speech in persons suffering from dry mouth.

SUMMARY OF THE INVENTION

The use of basic amino acids, e.g., arginine, in toothpaste formulations is known in the art, however, the inventors have discovered an unexpected and surprising result when toothpastes comprising arginine bicarbonate are used by persons suffering from xerostomia, that is, such compositions alleviate, treat, and inhibit dry mouth. It is believed that basic amino acids, e.g., arginine may be used to prevent cavities without or without fluoride, as basic amino acid salts, e.g., arginine-bicarbonate, in combination with an insoluble calcium salt, typically the dentifrice abrasive mimics the protective effects of saliva against caries and provides complete protection of the tooth enamel and roots by coating the tooth.

The invention thus comprises Composition 1.0, an oral care composition for the treatment, prevention, amelioration, or inhibition of dry mouth comprising an effective amount of a basic amino acid, e.g., arginine, in free or salt form, e.g., present in an amount of at least 1% (by weight of free base) where the formulation is a dentifrice or 0.1% where the formulation is a mouth rinse: the formulation optionally further comprising one or more of i. a calcium and/or phosphate ion source, e.g., calcium carbonate and/or a soluble calcium salt, e.g., calcium chloride, calcium lactate;
  ii. a soluble phosphate salt, e.g., potassium phosphate monobasic or dibasic potassium phosphate; and or
  iii. a calcium phosphate, e.g. dicalcium phosphate; a potassium ion source, e.g., potassium chloride, potassium phosphate monobasic or dibasic potassium phosphate, and/or potassium nitrate;
  iv. a fluoride source, e.g., a soluble fluoride salt, e.g., sodium fluoride or sodium monofluorophosphate;
  v. a magnesium source, e.g., magnesium chloride; a flavorant which induces saliva flow. e.g., capsacien; and/or
  vi. a polyol humectant, e.g., selected from glycerol, sugar alcohols (e.g., sorbitol, xylitol) and combinations thereof, for example any of the following compositions:

1.0.1. Composition 1.0 wherein the basic amino acid is arginine, lysine, citrullene, ornithine, creatine, histidine, diaminobutanoic acid, diaminoproprionic acid, salts thereof and/or combinations thereof.

1.0.2. Composition 1.0 or 1.0.1 wherein the basic amino acid has the L-configuration.

1.0.3. Any of the preceding compositions is provided in the form of a salt of a di- or tri-peptide comprising the basic amino acid.

1.0.4. Any of the preceding compositions wherein the basic amino acid is arginine.

1.0.5. Any of the preceding compositions wherein the basic amino acid is L-arginine.

1.0.6. Any of the preceding compositions wherein the basic amino acid is partially or wholly in salt form.

1.0.7. Composition 1.0.6 wherein the basic amino acid is arginine phosphate.

1.0.8. Composition 1.0.6 wherein the basic amino acid is in the form of arginine hydrochloride.

1.0.9. Composition 1.0.6 wherein the basic amino acid is arginine sulfate.

1.0.10. Composition 1.0.6 wherein the basic amino acid is arginine bicarbonate.

1.0.11. Any of the preceding compositions wherein a salt of the basic amino acid is formed in situ in the formulation by neutralization of the basic amino acid with an acid or a salt of an acid.

1.0.12. Any of the preceding compositions wherein the salt of the basic amino acid is formed by neutralization of the basic amino acid to form a premix prior to combination with the fluoride salt.

1.0.13. Any of the preceding compositions wherein the basic amino acid is present in an amount corresponding to about 0.1-20%, e.g., about 1 wt. % to about 10 wt. % of the total composition weight, the weight of the basic amino acid being calculated as free base form.

1.0.14. Composition 1.0.11 wherein the basic amino acid is present in an amount of about 7.5 wt. % of the total composition weight.
1.0.15. Composition 1.0.11 wherein the basic amino acid is present in an amount of about 5 wt. % of the total composition weight.
1.0.16. Composition 1.0.11 wherein the basic amino acid is present in an amount of about 3.75 wt. % of the total composition weight.
1.0.17. Composition 1.0.11 wherein the basic amino acid is present in an amount of about 1.5 wt. % of the total composition weight.
1.0.18. Any of the preceding compositions wherein the fluoride salt is stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.
1.0.19. Any of the preceding compositions wherein the fluoride salt is a fluorophosphate.
1.0.20. Any of the preceding composition wherein the fluoride salt is sodium monofluorophosphate.
1.0.21. Any of the preceding compositions where the fluoride salt is sodium fluoride.
1.0.22. Any of the preceding compositions wherein the fluoride salt is present in an amount of about 0.01 wt. % to about 2 wt. % of the total composition weight.
1.0.23. Any of the preceding compositions wherein the fluoride salt provides fluoride ion in an amount of about 0.1 to about 0.2 wt. % of the total composition weight.
1.0.24. Any of the preceding compositions wherein the soluble fluoride salt provides fluoride ion in an amount of from about 50 to 10,000 ppm.
1.0.25. Any of the preceding compositions which is a mouthwash having 100 to about 250 ppm available fluoride ion.
1.0.26. Any of the preceding compositions which is a dentifrice having about 750 to 2000 ppm available fluoride ion.
1.0.27. Any of the preceding compositions wherein the composition comprises 750 to 2000 ppm fluoride ion.
1.0.28. Any of the preceding compositions wherein the composition comprises 1.000 to 1500 ppm fluoride ion.
1.0.29. Any of the preceding compositions wherein the composition comprises about 1450 ppm fluoride ion.
1.0.30. Any of the preceding compositions wherein the pH is between about 6 and about 9, e.g., 6.5 and 7.4 or 7.5 and 9.
1.0.31. Any of the preceding compositions wherein the pH is between about 6.5 and about 7.4.
1.0.32. Any of the preceding compositions wherein the pH is between about 6.8 and about 7.2.
1.0.33. Any of the preceding compositions wherein the pH is approximately neutral.
1.0.34. Any of the preceding compositions further comprising an abrasive or particulate.
1.0.35. The immediately preceding composition wherein the adhesive or particulate is selected from sodium bicarbonate, calcium phosphate (e.g., dicalcium phosphate dihydrate), calcium sulfate, precipitated calcium carbonate, silica (e.g., hydrated silica), iron oxide, aluminum oxide, perlite, plastic particles, e.g., polyethylene, and combinations thereof.
1.0.36. The immediately preceding composition wherein the abrasive or particulate is selected from a calcium phosphate (e.g., dicalcium phosphate dihydrate), calcium sulfate, precipitated calcium carbonate, silica (e.g., hydrated silica), and combinations thereof.
1.0.37. Any of the preceding compositions comprising an abrasive in an amount of about 15 wt. % to about 70 wt. % of the total composition weight.
1.0.38. Any of the preceding compositions comprising a small particle abrasive fraction of at least 5% having a d50 of <5 micrometers.
1.0.39. Any of the preceding compositions having a RDA of less than 150, e.g., about 40-140.
1.0.40. Any of the preceding compositions wherein the anionic surfactant is selected from
  a. water-soluble salts of higher fatty acid monoglyceride monosulfates (e.g., the sodium salt of the monosulfated monoglyceride of hydrogenated coconut oil fatty acids such as sodium N-methyl N-cocoyl taurate, sodium cocomo-glyceride sulfate),
  b. higher alkyl sulfates, e.g., sodium lauryl sulfate,
  c. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K (for example sodium laureth-2 sulfate $(CH_3(CH_2)_{10}CH_2(OCH_2CH_2)_2OSO_3Na)$),
  d. higher alkyl aryl sulfonates (such as sodium dodecyl benzene sulfonate (sodium lauryl benzene sulfonate)),
  e. higher alkyl sulfoacetates (such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate),
  f. and mixtures thereof.
By "higher alkyl" is meant, e.g., $C_{6-30}$ alkyl. In particular embodiments, the anionic surfactant is selected from sodium lauryl sulfate and sodium ether lauryl sulfate.
1.0.41. Any of the preceding compositions wherein the anionic surfactant is selected from sodium lauryl sulfate, sodium ether lauryl sulfate, and mixtures thereof.
1.0.42. Any of the preceding compositions wherein the anionic surfactant is present in an amount of from about 0.3% to about 4.5% by weight.
1.0.43. Any of the preceding compositions additionally comprising surfactants selected from cationic, zwitterionic, and nonionic surfactants, and mixtures thereof.
1.0.44. Any of the preceding compositions comprising at least one humectant.
1.0.45. Any of the preceding compositions comprising at least one humectant selected from glycerin, sorbitol and combinations thereof.
1.0.46. Any of the preceding compositions comprising xylitol.
1.0.47. Any of the preceding compositions comprising at least one polymer.
1.0.48. Any of the preceding compositions comprising at least one polymer selected from polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum), and combinations thereof.
1.0.49. Any of the preceding compositions comprising gum strips or fragments.
1.0.50. Any of the preceding compositions comprising flavoring, fragrance and/or coloring.
1.0.51. Any of the preceding compositions comprising water.
1.0.52. Any of the preceding compositions comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, seabuckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.0.53. Any of the preceding compositions comprising an anti-inflammatory compound, e.g., an inhibitor of at least one of host pro-inflammatory factors selected from matrix metalloproteinases (MMP's), cyclooxygenases (COX) $PGE_2$, interleukin 1 (IL-1), IL-1β converting enzyme (ICE), transforming growth factor β1 (TGF-β1), inducible nitric oxide synthase (iNOS), hyaluronidase, cathepsins, nuclear factor kappa B (NF-κB), and IL-1 Receptor Associated Kinase (IRAK), e.g. selected from aspirin, ketorolac, flurbiprofen, ibuprofen, naproxen, indomethacin, aspirin, ketoprofen, piroxicam, meclofenamic acid, nordihydoguaiaretic acid, and mixtures thereof.

1.0.54. Any of the preceding compositions comprising an antioxidant, e.g., selected from the group consisting of Co-enzyme Q10, PQQ, Vitamin C, Vitamin E, Vitamin A, anethole-dithiothione, and mixtures thereof.

1.0.55. Any of the preceding compositions wherein the anti-microbial is poorly soluble.

1.0.56. Any of the preceding compositions comprising triclosan.

1.0.57. Any of the preceding compositions comprising triclosan and xylitol.

1.0.58. Any of the preceding compositions comprising triclosan, xylitol, and precipitated calcium carbonate.

1.0.59. Any of the preceding compositions comprising an antibacterial agent in an amount of 0.01-5 wt. % of the total composition weight.

1.0.60. Any of the preceding compositions comprising triclosan in an amount of 0.01 to 1 wt. percent of the total composition weight.

1.0.61. Any of the preceding compositions comprising triclosan in an amount of about 0.3% of the total composition weight.

1.0.62. Any of the preceding compositions comprising a whitening agent.

1.0.63. Any of the preceding compositions comprising a whitening agent selected from a whitening active selected from the group consisting of peroxides, metal chlorites, perborates, percarbonates, peroxyacids, hypochlorites, and combinations thereof 1.0.64. Any of the preceding compositions comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate).

1.0.65. Any of the preceding compositions further comprising an agent that interferes with or prevents bacterial attachment, e.g., solbrol or chitosan.

1.0.66. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate.

1.0.67. Any of the preceding compositions further comprising a soluble calcium salt, e.g., selected from calcium sulfate, calcium chloride, calcium nitrate, calcium acetate, calcium lactate, and combinations thereof.

1.0.68. Any of the preceding compositions further comprising a physiologically acceptable potassium salt, e.g., potassium nitrate or potassium chloride, in an amount effective to reduce dentinal sensitivity.

1.0.69. Any of the preceding compositions comprising from about 0.1% to about 7.5% of a physiologically acceptable potassium salt, e.g., potassium nitrate and/or potassium chloride.

1.0.70. Any of the preceding compositions which is a toothpaste comprising an arginine salt, e.g., arginine hydrochloride, arginine phosphate or arginine bicarbonate; triclosan; an anionic surfactant, e.g., sodium lauryl sulfate; and a soluble fluoride salt e.g., sodium monofluorophosphate or sodium fluoride.

1.0.71. Any of the preceding compositions effective upon application to the oral cavity, e.g., with brushing, to reduce dry mouth and/or to generate a perception of hydrating effects, and optionally to (i) reduce or inhibit formation of dental caries, e.g., caries which result from reduced saliva flow and dry mouth, (ii) reduce, repair or inhibit early enamel lesions, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolylic bacteria, (ix) inhibit microbial biofilm formation in the oral cavity, (x) raise and/or maintain plaque pH at levels of at least pH 5.5 following sugar challenge, (xi) reduce plaque accumulation, (xiii) enhance systemic health, including cardiovascular health, e.g., by reducing potential for systemic infection via the oral tissues, and/or (xiv) reduce erosion of the teeth, (xv) whiten the teeth, (xvi) immunize the teeth against cariogenic bacteria, (xvii) clean the teeth and oral cavity, and (xviii) reduce sleep disruption due to dry mouth.

1.0.72. A composition obtained or obtainable by combining the ingredients as set forth in any of the preceding compositions.

1.0.73. Any of the preceding compositions in a form selected from mouthrinse, toothpaste, tooth gel, tooth powder, non-abrasive gel, mousse, foam, mouth spray, lozenge, oral tablet, dental implement, and pet care product.

1.0.74. Any of the preceding compositions wherein the composition is toothpaste.

1.0.75. Any of the preceding compositions wherein the composition is a toothpaste optionally further comprising one or more of one or more of water, abrasives, surfactants, foaming agents, vitamins, polymers, enzymes, humectants, thickeners, antimicrobial agents, preservatives, flavorings, colorings and/or combinations thereof.

1.0.76. Any of the preceding compositions 1.0-1.0.72 wherein the composition is a mouthwash.

1.0.77. Any of the preceding compositions 1.0-1.0.72 wherein the composition is a chewing gum.

1.0.78. Any of the preceding compositions further comprising a breath freshener, fragrance or flavoring.

Levels of active ingredients will vary based on the nature of the delivery system and the particular active. For example, the basic amino acid may be present at levels from, e.g., about 0.1 to about 20 wt % (expressed as weight of free base), e.g., about 0.1 to about 3 wt % for a mouthrinse, about 1 to about 10 wt % for a consumer toothpaste or about 7 to about 20 wt % for a professional or prescription treatment product, fluoride may be present at levels of, e.g., about 25 to about 25,000 ppm, for example about 25 to about 250 ppm for a mouthrinse, about 750 to about 2,000 ppm for a consumer toothpaste, or about 2,000 to about 25,000 ppm for a professional or prescription treatment product. Levels of antibacterial will vary similarly, with levels used in toothpaste being e.g., about 5 to about 15 times greater than used in mouthrinse. For example, a triclosan mouthrinse may contain, e.g., about 0.03 wt % triclosan white a triclosan toothpaste may contain about 0.3 wt % triclosan.

The present invention also includes Method 2.0, a method for treating, inhibiting or relieving dry mouth comprising introducing into the oral cavity to a patient in need thereof, e.g., suffering from dry mouth, an oral care composition comprising a basic amino acid in free or salt form, e.g., any one of compositions 1.0-1.0.78.

Additional embodiments of the present invention also include the following methods:

2.1 Of method 2.0, wherein the method is also effective (i) reduce or inhibit formation of dental caries, (ii) reduce, repair or inhibit early enamel lesions, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xiii) enhance systemic health, including cardiovascular health, e.g., by reducing potential for systemic infection via the oral tissues, and/or (xiv) reduce erosion of the teeth, and/or (xv) clean the teeth and oral cavity.

2.2 Of methods 2.0 or 2.2 wherein the composition comprises at least 7.5% arginine.

2.3 Of methods 2.0-2.2 wherein the composition comprises at least 1.0% arginine bicarbonate.

2.4 Of methods 2.0-2.3 wherein the composition comprises at least 5% of a humectant 2.5 Of methods 2.0-2.4 wherein the patient is predisposed to dry mouth, 2.6 Of methods 2.0-2.5 wherein the patient is suffering from dry mouth.

2.7 Of methods 2.0-2.6 wherein the patient has difficulty masticating food stuff as a result of dry mouth.

2.8 Of methods 2.0-2.7 wherein the patient has difficulty swallowing as a result of dry mouth.

2.9 Of methods 2.0-2.8 wherein the patient has speech difficulties as a result of dry mouth.

2.10 Of methods 2.0-2.9 wherein the patient also suffers from opportunistic infection of the tongue as a result of dry mouth.

2.11 Of methods 2.0-2.10 wherein, dry mouth is caused by a disease.

2.12 Of methods 2.0-2.11 wherein the patient is being treated with a medicament, said medicament causing said dry mouth.

2.13 Of methods 2.0-2.12 wherein dry mouth is chronic.

2.14 Of methods 2.0-2.13 wherein the composition comprises from about 7.5% to about 25.0% arginine.

2.15 Of methods 2.0-2.14 wherein the composition is a dentifrice.

2.16 Of methods 2.0-2.15 wherein the composition is a toothpaste.

2.17 Of methods 2.0-2.16 wherein the composition is a gel.

2.18 Of methods 2.0-2.17 wherein the composition is applied in the oral cavity with a tooth brush.

2.19 Of methods 2.0-2.15 wherein the composition is a mouth wash.

2.20 Of methods 2.0-2.19 wherein the patient performs the method more than once a day.

2.21 Of methods 2.0-2.20 wherein the patient performs the method daily.

The present invention also contemplates the use of a basic amino acid in free or salt form, e.g., arginine, e.g., as provided in any of compositions 1.0-1.0.78, for the treatment, amelioration, inhibition, and/or prevention, of dry mouth.

The present invention further provides the use of a basic amino acid, in free or salt form, for the manufacture of a medicament for treating, ameliorating, inhibiting or preventing dry mouth.

The present invention further provides a basic amino acid, in tree or salt form, for use in the treatment, amelioration, inhibition or prevention of dry mouth.

DETAILED DESCRIPTION OF THE INVENTION

The present invention provides methods and compositions for the treatment, prevention, management, or inhibition of xerostomia in a patient suffering therefrom, in one embodiment, the patient, suffers from, or is predisposed to xerostomia by disease or injury. In another embodiment, the patient suffers from, or is predisposed to xerostomia by treatment(s) of medicaments which cause xerostomia, wherein the dry mouth is a side effect of the medicament.

The term "Treat" or "ameliorate" is used herein to mean that administration of a composition of the present invention mitigates a condition in the patient, preferably a mammal, more preferably, a human.

The term "inhibit" is used herein to mean that administration of a composition of the present invention delays the onset of a condition, e.g., by 6 hours, 12 hours. 24 hours, 48 hours, or 96 hours following the administration of the composition.

The term "prevent" does not imply that a particular condition will be completely avoided in the future, rather, that the particular condition will be avoided until the patient is able to administer the compositions of the present invention at a second time point, e.g., within 12 hours, 24 hours, 48 hours, or 96 hours of an initial administration.

Without intending to be bound by a particular theory, it is hypothesized that a significant factor in the beneficial effect of arginine is that arginine may be metabolized by certain types of bacteria, e.g., *S. sanguis* which are not cariogenic and which compete with cariogenic bacteria such as *S. mutans*, for position on the teeth and in the oral cavity. The arginolytic bacteria can use arginine and other basic amino acids to produce ammonia, thereby raising the pH of their environment, while cariogenic bacteria metabolize sugar to produce lactic acid, which tends to lower the plaque pH and demineralize the teeth, ultimately leading to cavities. It is believed that regular use of a Composition of the Invention, over time, will lead to a relative increase in the arginolytic bacteria and a relative decrease in the cariogenic bacteria, resulting in a higher plaque pH (notwithstanding that the Composition of the Invention is itself generally pH neutral, the basic amino acid having been neutralized by an inorganic oxoacid). It is believed, that this pH-raising effect may be accomplished in compositions which are substantially free of fluoride. It is also believed that this pH-raising effect may be mechanistically separate from and complementary to the effect of fluoride in promoting remineralization and strengthening the tooth enamel.

Concentrations of arginine in oral care compositions for anti-caries effect may be about 1.5%. Higher concentrations of arginine may be utilized for sensitive tooth relief e.g., from about 3.75% to about 7.50% arginine, as the formulations physically occlude open dentinal tubules (pathways to pain), and provide effective pain relief. Without being bound by theory, it is hypothesized that even higher levels of arginine, e.g., greater than 7.50%, that is, from about 7.50% to about 25%, from about 8.0% to about 20%, from about 9% to about 15%, or about 10% coat teeth, gums, and/or the oral cavity, leaving a perception that the mouth has been moisturized or hydrated.

Compositions of the present invention may be in the form of a dentifrice comprising additional ingredients selected from one or more of water, abrasives, surfactants, foaming agents, vitamins, polymers, enzymes, humectants, thickeners, antimicrobial agents, preservatives, flavorings, colorings and/or combinations thereof.

The basic amino acids which can be used in the compositions and methods of the invention include not only naturally occurring basic amino acids, such as arginine, lysine, and histidine, but also any basic amino acids having a carboxy 1 group and an amino group in the molecule, which are water-soluble and provide an aqueous solution with a pH of 7 or greater. Accordingly, basic amino acids include, but are not limited to, arginine, lysine, citrullene, ornithine, creatine, histidine, diaminobutanoic acid, diaminoproprionic acid, salts thereof or combinations thereof. In a particular embodiment, the basic amino acids are selected from arginine, citrullene, and ornithine. In certain embodiments, the basic amino acid is arginine, for example, L-arginine, or a salt thereof.

The compositions of the invention are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

In various embodiments, the basic amino acid is present in an amount of about 7.5 wt. % to about 25 wt. % of the total composition weight, about 1 wt. % to about 10 wt. % of the total composition weight, for example about 1.5 wt. %, 3.75 wt. %. 5 wt. %, or 7.5 wt. % of the total composition weight.

The oral care compositions may further include one or more fluoride ion sources, e.g., soluble fluoride salts. A wide variety of fluoride ion-yielding materials can be employed as sources of soluble fluoride in the present compositions, and such materials are known to those of skill in the art, Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al, incorporated herein by reference.

Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof.

In certain embodiments, the oral care composition of the invention may also contain a source of fluoride ions or fluorine-providing ingredient in amounts sufficient to supply about 25 ppm to 25,000 ppm of fluoride ions, generally at least about 500 ppm. e.g., about 500 to about 2000 ppm, e.g., about 1000 to about 1600 ppm, e.g., about 1450 ppm. The appropriate level of fluoride will depend on the particular application. A mouthwash, for example, would typically have about 100 to about 250 ppm fluoride, A toothpaste for general consumer use would typically have about 1000 to about 1500 ppm, with pediatric toothpaste having somewhat less. A dentifrice or coating for professional application could have as much as 5,000 or even 25,000 ppm fluoride.

In certain embodiments, the oral care composition of the invention may contain a source of fluoride ions or fluorine-providing ingredient in amounts sufficient to supply about 100 ppm to 10,000 ppm of fluoride ions, e.g., 1000-2000 ppm.

The Compositions of the Invention may comprise a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate.

The compositions may include one or more additional abrasives known by those of skill in the art, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcinated alumina, bentonite or other siliceous materials, or combinations thereof.

The silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference.

In certain embodiments, abrasive materials useful in the practice of the oral care compositions in accordance with the invention include silica gels and precipitated amorphous silica having an oil absorption value of about less than 1.00 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns.

In particular embodiments, the particulate or abrasive materials comprise a large fraction of very small particles, e.g., having a d50 less than about 5 microns, for example small particle silica (SPS) having a d50 of about 3 to about 4 microns, for example Sorbosil AC43® (Ineos). Such small particles are particularly useful in formulations targeted at reducing hypersensitivity. The small particle component may be present in combination with a second larger particle abrasive, in certain embodiments, for example, the formulation comprises about 3 to about 8% SPS and about 25 to about 45% of a conventional abrasive.

Low oil absorption silica abrasives particularly useful in the practice of the invention are marketed under the trade designation Sylodent XWA® by Davison Chemical Division of W.R. Grace & Co, Baltimore, Md. 21203. Sylodent 650 XW®, a silica hydrogel composed of particles of colloidal silica having a water content of about 29% by weight averaging about 7 to about 10 microns in diameter, and an oil absorption of less than about 70 cc/100 g of silica is an example of a low oil absorption silica abrasive useful in the practice of the present invention. The abrasive is present in the oral care composition of the present invention at a concentration of about 10 to about 60% by weight, in other embodiment about 20 to about 45% by weight, and in another embodiment about 30 to about 50% by weight.

The oral care compositions of the invention also may include an agent to increase the amount of foam that is produced when the oral cavity is brushed. Such agents are known to those of skill in the art. Illustrative examples of agents that increase the amount of foam include, hut are not limited to polyoxyethylene and certain polymers including, but not limited to, alginate polymers.

The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide.

The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2% by weight.

Another agent optionally included in the oral care composition of the invention is a surfactant or a mixture of compatible surfactants. Suitable surfactants are those which are reasonably stable throughout a wide pH range, for example, anionic, cationic, nonionic or zwitterionic surfactants. Suitable surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference. A preferred surfactant is sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

The oral care compositions of the invention may also include a flavoring agent. Flavoring agents which are used in the practice of the present invention are known by those of skill in the art, and may include essential oils as well as various flavoring agents, esters, alcohols, and similar materials. The flavoring agent is incorporated in the oral composition at a concentration of about 0.1 to about 5% by weight and about 0.5 to about 1.5% by weight. The dosage of flavoring agent in the individual oral care composition dosage (i.e., a single dose) is about 0.001 to 0.05% by weight and in another embodiment about 0.005 to 0.015% by weight.

The oral care compositions and methods of the invention also may optionally include one or more chelating agents able to complex calcium found in the cell wall of the bacteria. Binding of this calcium weakens the bacterial ceil wall and augments bacterial lysis. Chelating agents are well known by those of skill in the art. e.g., soluble pyrophosphates, either in hydrated or unhydrated forms. An effective amount of pyrophosphate salt useful in the present composition is generally enough to provide at least 1.0 wt. % pyrophosphate ions, about 1.5 wt. % to about 6 wt. %, about 3.5 wt. % to about 6 wt. % of such ions.

The oral care compositions or methods of the invention also optionally include one or more polymers, which are known by those of skill in the art. Such polymers may include polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum). Polymers suitable for use may include Gantrez AN 139 (M.W. 500,000), AN 119 (M.W. 250,000) and S-97 Pharmaceutical Grade (M.W. 70,000), of GAF Chemicals Corporation. Suitable polymers may also include homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference. Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

The compositions and methods of the present invention may also comprise thickening material to provide a desirable consistency or to stabilize or enhance the performance of the formulation. Such thickening materials are known by those of skill in the art, e.g., carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

The compositions and methods of the present invention may also optionally include one or more enzymes. Useful enzymes include those known by those of skill in the art, and may include proteases, glucanohydrolases, endoglycosidases, amylases, mutanases, lipases and mucinases or compatible mixtures thereof. Enzymes suitable for use in the present invention are disclosed in U.S. Pat. No. 5,000,939 to Dring et al, U.S. Pat. Nos. 4,992,420; 4,355,022; 4,154,815; 4,058,595; 3,991,177; and 3,696,191 all incorporated herein by reference. An enzyme of a mixture of several compatible enzymes in the current invention constitutes about 0.002% to about 2.0% in one embodiment or about 0.05% to about 1.5% in another embodiment or in yet another embodiment about 0.1% to about 0.5%.

Water may also be present in the oral compositions of the invention. Water, employed in the preparation of commercial oral compositions is preferably deionized and free of organic impurities. Water commonly makes up the balance of the compositions, and includes the free water which is added plus that amount which is introduced with other materials such as with sorbitol or any components of the invention.

The present invention may comprise humectant to prevent the composition from hardening upon exposure to air, and to aid in the hydration of the mouth. Certain humectants can also impart desirable sweetness or flavor to dentifrice compositions. The humectant, on a pure humectant basis, generally includes about 15% to about 70% in one embodiment or about 30% to about 65% in another embodiment by weight of the dentifrice composition.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

In addition to the above described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

The compositions and methods according to the invention are useful to a method to treat dry mouth, and optionally protect the teeth by facilitating repair and remineralization, in particular to reduce or inhibit formation of dental caries, reduce or inhibit demineralization and promote remineralization of the teeth, reduce hypersensitivity of the teeth, and reduce, repair or inhibit pre-carious lesions of the enamel, e.g., as detected by quantitative light-induced fluorescence (QLF) or electrical caries measurement (ECM). Quantitative light-induced fluorescence is a visible light system that permits early detection of pre-caries lesions in the enamel. Normal teeth fluoresce in visible light; demineralized teeth do not or do so only to a lesser degree. The area of demineralization can be quantified and its progress monitored. Electrical conductance measurement exploits the fact that the fluid-filled tubules exposed upon demineralization and erosion of the enamel conduct electricity. An increase in the conductance of the patient's teeth therefore may indicate demineralization. The Compositions of the Invention are thus useful in a method to reduce pre-carious lesions of the enamel (as measured by QLF or ECM) relative to a composition lacking effective amounts of fluorine and/or arginine.

As such the Compositions of the Invention are useful not only for treating dry mouth, but also for treating other oral conditions in the mouth, and to clean the oral cavity and provide improved methods of promoting oral health.

Enhancing oral health also provides benefits in systemic health, as the oral tissues can be gateways for systemic infections. Good oral health is associated with systemic health, including cardiovascular health. The compositions and methods of the invention provide particular benefits because basic amino acids, especially arginine, are sources of nitrogen which supply NO synthesis pathways and thus enhance microcirculation in the oral tissues. Providing a less acidic oral environment is also helpful in reducing gastric distress and creates an environment less favorable to Heliobacter, which is associated with gastric ulcers. Arginine in particular is required for high expression of specific immune cell receptors, for example T-cell receptors, so that arginine can enhance an effective immune response. The compositions and methods of the invention are thus useful to enhance systemic health, including cardiovascular health.

The compositions and methods according to the invention can be incorporated into oral compositions for the care of the mouth and teeth such as toothpastes, transparent pastes, gels, mouth rinses, sprays and chewing gum.

As used throughout, ranges are used as shorthand for describing each and every value that is within the range. Any value within the range can be selected as the terminus of the range, in addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

Example 1—Toothpaste Formulation

A toothpaste composition is prepared from the following ingredients to produce a toothpaste having 7.50% wt. arginine.

| | |
|---|---|
| Deionized Water | 7.400 |
| Glycerin | 21.000 |
| Carboxymethyl cellulose | 0.500 |
| Saccharin | 0.250 |
| Basic amino acid salt (arginine bicarbonate) | 10.000 |
| Calcium carbonate | 29.000 |
| Hydrated silica | 31.000 |
| Flavor | 0.750 |
| Color solution (1% FD&C Blue #1) | 0.100 |

Example 2—Patient Study

Eight patients suffering from dry mouth are provided with the composition of EXAMPLE 1. The patients are instructed to brush with the composition of EXAMPLE 1 twice a day, and record observations on their dry mouth condition prior to usage, at day 4, and at day 8.

Prior to use of the toothpaste, 7 patients suffer from dry mouth throughout the whole day: four patients also suffer from dry lips and tongue; two patients have difficulty swallowing; 3 patients have difficulty eating, talking and sleeping due to dry mouth.

At day 4, most patients feel the composition hydrates their mouth, and left the mouth feeling comfortable. No patient thinks the composition made the mouth drier. 25% of patients indicate that the mouth felt smooth, moist, and hydrated.

At day 8, most patients believe the composition provides dry mouth relief, leaving their mouth feeling moist, pleasant and smooth.

Example 3—Artificial Saliva Formulation Comprising Arginine

An artificial saliva formulation is prepared from the following ingredients:

| RAW MATERIAL | WEIGHT % |
|---|---|
| Deionized Water | 96.26815 |
| Xylitol | 2.00000 |
| L-Arginine | 0.50000 |
| Hydroxyethyl cellulose | 0.43000 |
| Flavor | 0.40000 |
| Methyl paraben | 0.20000 |
| Dibasic potassium phosphate | 0.08000 |
| Potassium chloride | 0.06200 |
| Potassium phosphate monobasic | 0.04300 |
| Calcium chloride dihydrate | 0.01000 |
| Magnesium chloride | 0.00590 |
| Food colorant | 0.00050 |
| Sodium fluoride | 0.00045 |
| TOTAL | 100.00000 |

The invention claimed is:

1. A method to treat, ameliorate, inhibit, or prevent dry mouth in a person that either has xerostomia, is diagnosed with a disease or injury that predisposes the person to xerostomia or is being treated with a medication that predisposes the person to xerostomia, the method comprising administering to the oral cavity of the person a composition comprising a basic amino acid, in free or salt form, and zinc citrate;
   wherein the basic amino acid is arginine or arginine bicarbonate, and the arginine is L-arginine; and
   wherein the composition further comprises one or more compounds selected from the group consisting of:
   (a) a calcium ion source;
   (b) a phosphate ion source;
   (c) a potassium ion source;
   (d) a magnesium ion source;
   (e) a fluoride ion source;
   (f) a flavorant which promotes saliva flow; and
   (g) a polyol humectant; and
   wherein the fluoride ion source is selected from stannous fluoride, sodium fluoride, potassium fluoride, sodium monofluorophosphate, sodium fluorosilicate, ammonium fluorosilicate, amine fluoride, ammonium fluoride, and combinations thereof, and
   wherein the composition has a pH between about 6.8 and 7.2.

2. The method of claim 1 wherein dry mouth is chronic.

3. The method of claim 1 wherein the composition is a dentifrice.

4. The method of claim 1 wherein the composition is a mouth rinse.

5. The method of claim 4 wherein the mouth rinse is an artificial saliva further comprising one or more of: a fluoride ion source, a calcium ion source, a phosphate ion source, a potassium ion source, and combinations thereof.

6. The method of claim 3, wherein the one or more compounds is a combination of a calcium ion source and a polyol humectant.

7. The method of claim 6, wherein the basic amino acid is arginine bicarbonate in an amount from about 0.1% to about 20% by weight and the polyol humectant is present in an amount from 15% to about 70% by weight.

8. The method of claim 7, wherein
   the calcium ion source is selected from the group consisting of calcium carbonate, calcium chloride, calcium lactate, dicalcium phosphate and combinations thereof; and
   the polyol humectant is selected from the group consisting of glycerol, sugar alcohols, sorbitol, xylitol and combinations thereof.

9. The method of claim 8, wherein the calcium ion source is calcium carbonate and the composition further comprises a carboxymethylcellulose and a hydrated silica.

10. The method of claim 9, wherein the polyol humectant is glycerol.

11. The method of claim 4, wherein the one or more compounds is a combination of a calcium ion source, a phosphate ion source, a potassium ion source, a magnesium ion source, a fluoride ion source and a polyol humectant.

12. The method of claim 11, wherein the basic amino acid is arginine in an amount from about 0.1% to about 20% by weight and the polyol humectant is present in an amount from 15% to about 70% by weight.

13. The method of claim 12, wherein
   the calcium ion source is selected from the group consisting of calcium carbonate, calcium chloride, calcium lactate, dicalcium phosphate and combinations thereof;
   the phosphate ion source is selected from potassium phosphate monobasic, dibasic potassium phosphate, dicalcium phosphate, sodium monofluorophosphate and combinations thereof;
   the potassium ion source is selected from the group consisting of potassium nitrate, potassium chloride, potassium phosphate monobasic, dibasic potassium phosphate and combinations thereof;

the magnesium ion source is magnesium chloride; and the polyol humectant is selected from the group consisting of glycerol, sugar alcohols, sorbitol, xylitol and combinations thereof.

14. The method of claim 13, wherein the calcium ion source is calcium chloride;

the phosphate ion source comprises potassium phosphate monobasic; and the potassium ion source is potassium chloride.

15. The method of claim 14, wherein the phosphate ion source further comprises dibasic potassium phosphate; and the composition further comprises a hydroxyethyl cellulose.

16. The method of claim 15, wherein the polyol humectant is xylitol.

\* \* \* \* \*

UNITED STATES PATENT AND TRADEMARK OFFICE
CERTIFICATE OF CORRECTION

PATENT NO. : 10,471,283 B2
APPLICATION NO. : 12/866630
DATED : November 12, 2019
INVENTOR(S) : Rajnish Kohli et al.

It is certified that error appears in the above-identified patent and that said Letters Patent is hereby corrected as shown below:

On the Title Page

Item (56), Column 2, under "OTHER PUBLICATIONS", Line 6, delete "Machado et al." and insert -- Machado et al., --, therefor.

On Page 2, Item (56), Column 2, under "OTHER PUBLICATIONS", Line 1, delete "Chatterjee et al,." and insert -- Chatterjee et al., --, therefor.

On Page 2, Item (56), Column 2, under "OTHER PUBLICATIONS", Line 7, delete "Med,." and insert -- Med., --, therefor.

In the Specification

In Column 3, Line 44, delete "1.000" and insert -- 1000 --, therefor.

In Column 6, Line 42, delete "arginolylic" and insert -- arginolytic --, therefor.

In Column 7, Line 14, delete "product, fluoride" and insert -- product. Fluoride --, therefor.

In Column 7, Line 23, delete "white" and insert -- while --, therefor.

In Column 8, Line 35, delete "tree" and insert -- free --, therefor.

In Column 9, Line 42, delete "carboxy 1" and insert -- carboxyl --, therefor.

In Column 11, Line 9, delete "1.00" and insert -- 100 --, therefor.

In Column 11, Line 31, delete "XW®" and insert -- XWA® --, therefor.

In Column 11, Line 45, delete "hut" and insert -- but --, therefor.

Signed and Sealed this
Thirty-first Day of March, 2020

Andrei Iancu
*Director of the United States Patent and Trademark Office*

CERTIFICATE OF CORRECTION (continued)
U.S. Pat. No. 10,471,283 B2

In Column 12, Line 20, delete "agents," and insert -- aldehydes, --, therefor.

In Column 12, Line 30, delete "wall" and insert -- walls --, therefor.

In Column 12, Line 31, delete "ceil" and insert -- cell --, therefor.

In Column 13, Line 56, delete "ail" and insert -- all --, therefor.

In Column 13, Line 62, delete "demineraiization" and insert -- demineralization --, therefor.

In Column 14, Line 4, delete "demineraiization" and insert -- demineralization --, therefor.

In Column 14, Line 6, delete "demineraiization" and insert -- demineralization --, therefor.

In Column 14, Line 9, delete "demineraiization." and insert -- demineralization. --, therefor.